United States Patent [19]

Norton

[11] 4,139,306

[45] Feb. 13, 1979

[54] TELEVISION INSPECTION SYSTEM

[75] Inventor: James F. Norton, Alplaus, N.Y.

[73] Assignee: General Electric Company, Schenectady, N.Y.

[21] Appl. No.: 766,615

[22] Filed: Feb. 7, 1977

[51] Int. Cl.² .................. H04N 7/02; G01N 21/32
[52] U.S. Cl. ................................. 358/106; 356/430
[58] Field of Search .............. 356/200, 199, 210, 237; 250/572, 562, 563; 358/106, 107

[56] References Cited

U.S. PATENT DOCUMENTS 2,648,723  8/1953  Goldsmith ................... 358/106X
3,746,784  7/1973  Van Oosterhout ............. 358/106

Primary Examiner—Vincent P. McGraw
Assistant Examiner—Rodney B. Bovernick
Attorney, Agent, or Firm—Geoffrey H. Krauss; Joseph T. Cohen; Marvin Snyder

[57] ABSTRACT

A television inspection system for detecting flaws on a cable and the like, without contact, utilizes means for obliquely, evenly illuminating the object; a backing member having the same average reflectivity as the object and video sensor-signal processing means for detecting changes in the reflected illumination to sense flaws upon the object's surface.

10 Claims, 7 Drawing Figures

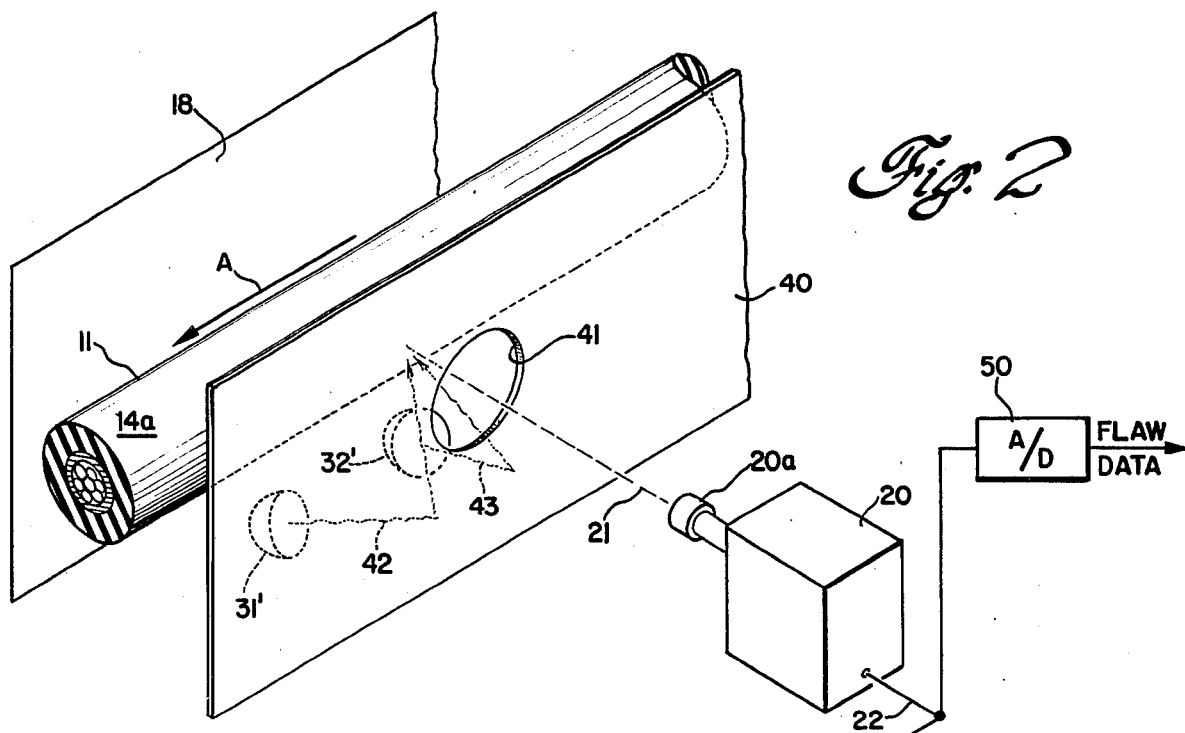
Fig. 2
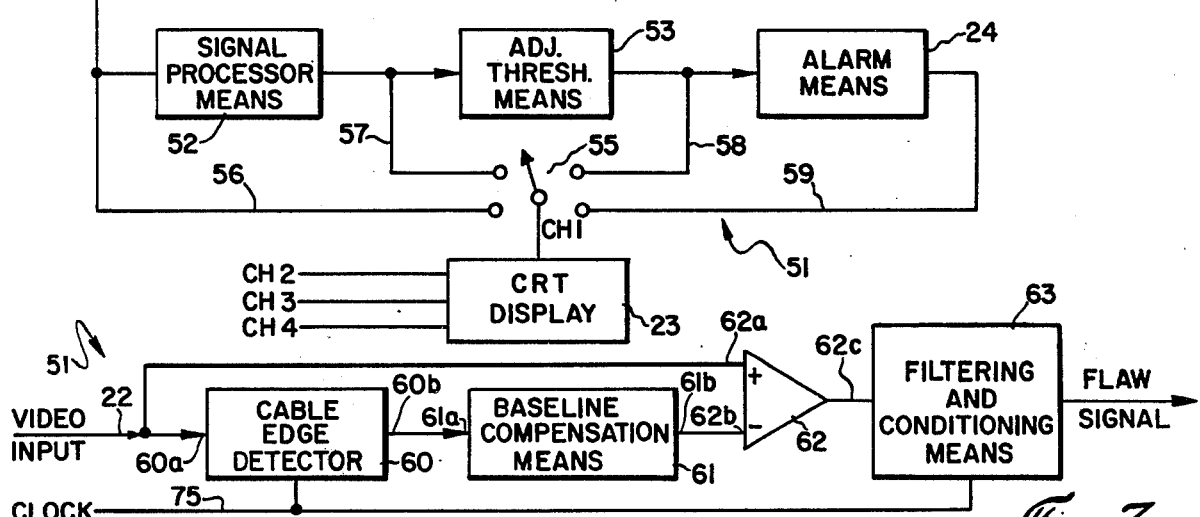
Fig. 3
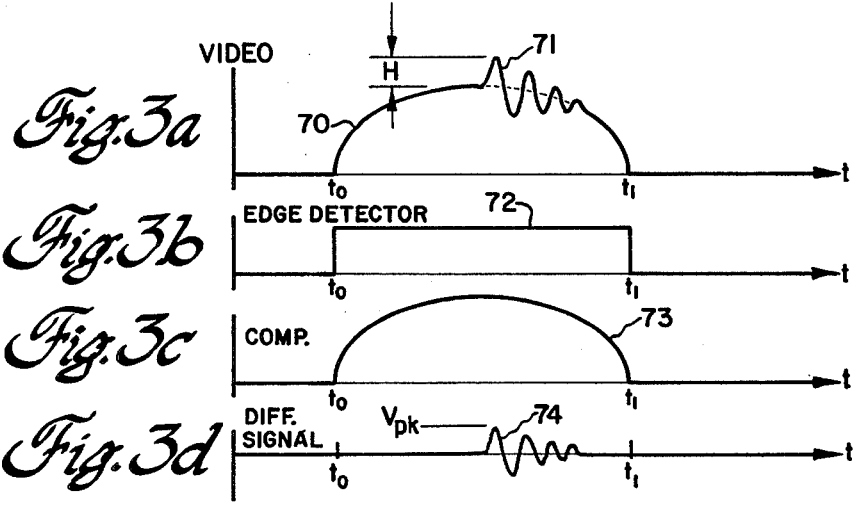
Fig. 3a
Fig. 3b
Fig. 3c
Fig. 3d

4,139,306

TELEVISION INSPECTION SYSTEM

BACKGROUND OF THE INVENTION

The present invention relates to flaw detection, and more particularly, to a novel surface flaw detection system utilizing video sensing and processing apparatus.

The manufacture of many objects requires detection of flaws on the object's surface, particularly by apparatus which does not contact the object to be tested, to prevent damage to the object. Illustratively, in the construction of a high voltage cable, successive layers of extruded plastic insulation are fabricated over a conductive core; it is necessary to detect voids and other surface flaws, such as indentations, scrapes, pits and the like, on the insulation layer surface, to prevent possible corona effects and breakdown failure of the cable between the conductive core and an exterior-wound conductive jacket. Traditionally, inspection of the surface of the cable insulation was performed, prior to exterior conductive layer fabrication, by visual or tactile inspection. Detection of minute flaws is highly improbable, especially if the object is moving at any appreciable velocity past the observer. An automatic system for detecting surface flaws, with high probability of generating an alarm for flaws exceeding a preselected set of characteristics, is highly desirable.

BRIEF SUMMARY OF THE INVENTION

In accordance with the invention, a system for detecting surface flaws by video sensing and processing, utilizes a television camera receiving light from a portion of the surface of an object to be analyzed. The object is backed by a backing member having the same average reflectivity as the object surface. The object and the backing member are illuminated, in one preferred embodiment, both by a diffuse light source emitting from a direction close to the viewing axis of the video sensor, and by several sources of illumination arranged oblique to the surface of the object, i.e., at an angle to the lens axis of the video sensor, to reflect light from the edges of flaws for varying the video signal obtained as the object moves past the illumination means and the video sensor. Video processing means having an adjustable threshold and alarm means are utilized to detect light reflections of a magnitude corresponding to flaws exceeding a predetermined set of limits.

Accordingly, it television an object of the present invention to provide a televison system for detecting flaws upon the surface of an object moving past an optical axis of a video sensor.

This and other objects of the present invention will become apparent upon consideration of the following detailed description and the corresponding drawings.

BRIEF DESCRIPTION OF THE DRAWINGS

FIG. 2 is a partially-schematic perspective view of another preferred embodiment of TV flaw inspection systems, illustrating one possible signal processing subsystem for use therewith;

FIG. 3 is a schematic block diagram of one preferred embodiment of signal processing means for use in a TV flaw detection system; and FIGS. 3a–3d are a set of coordinated graphs illustrating the operation of the signal processing subsystem of FIG. 3.

DETAILED DESCRIPTION OF THE INVENTION

Figure 1:
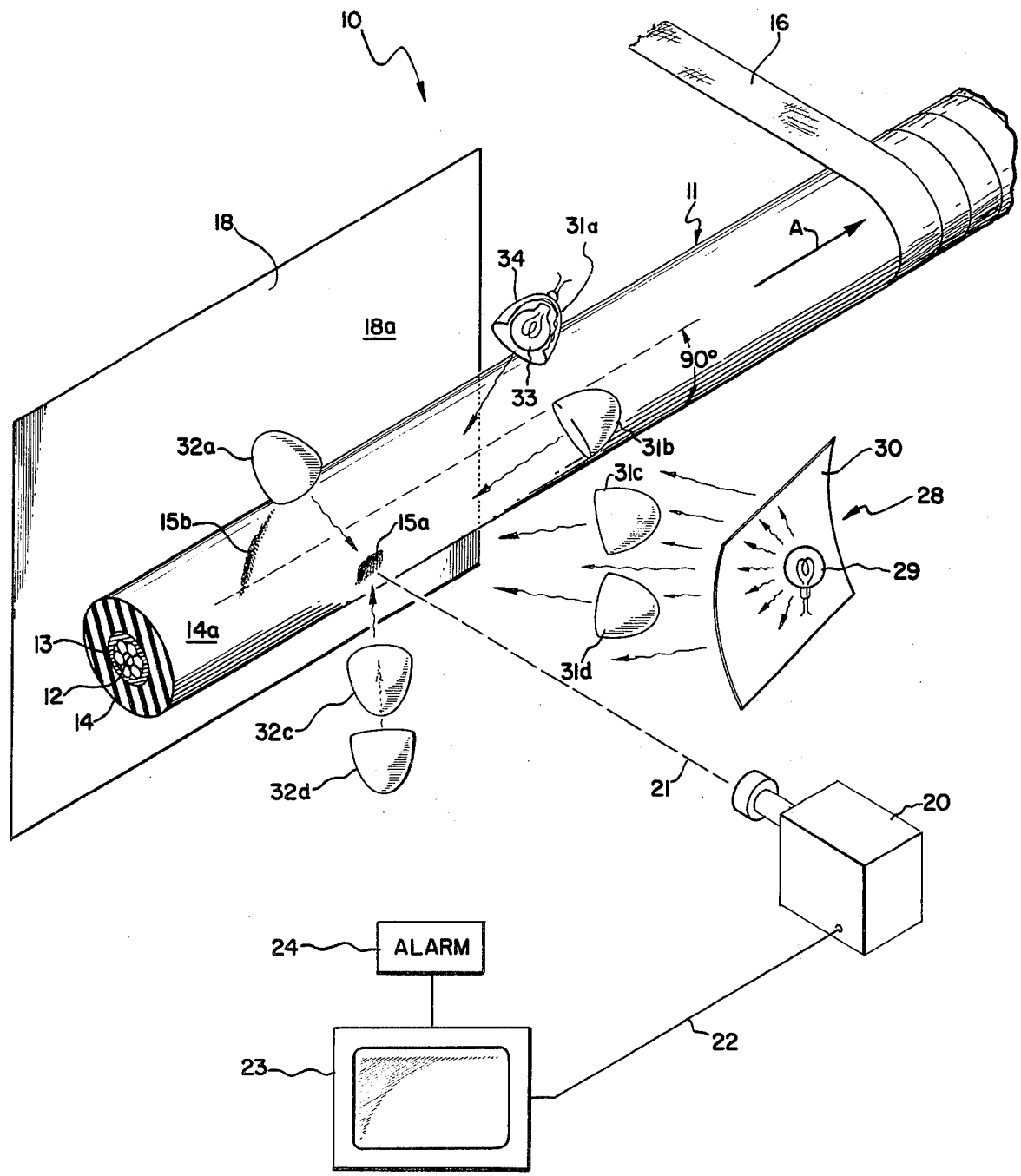
FIG. 1 is a perspective view of one preferred embodiment of a television inspection system for flaw detection in accordance with the principles of the present invention.

Referring initially to FIG. 1, television flaw detection system 10 is utilized to test an object 11, such as a high voltage electric cable formed with a core 12 of stranded wire positioned within a cylindrical inner conductor 13 and encased in an annular layer 14 of insulating material. The possibility exists that flaws 15a, 15b will be formed as indentations, scrapes, pits and the like upon the exterior surface 14a of the insulation. It is desired to detect flaws 15 on the object surface before the flaws, moving in the direction of arrow A, are subsequently hidden beneath an outer covering 16, such as a conductive tape and the like. Flaw detection allows correction before a decrease in the effective insulation between the conductive inner cylinder 13 and the conductive outer covering 16 is facilitated, preventing subsequent production of corona and insulation breakdown failures when the high voltage cable is utilized in its intended environment.

Object 11 is placed in front of a backing member 18 having the same average reflectivity as the surface 14a of the cable, e.g. if the cable insulation is of a dull black color having an average reflectivity R, then the backing member surface 18a facing object 11 must also be of the same dull black color and have the same average reflectivity R.

A video sensor means, such as television camera 20 and the like, is placed adjacent to the moving object 11 and on the opposite side of the object from the backing member. The sensor means is aligned with the central axis 21 of its field of view centered upon the object. Typically, such alignment allows a 90° section of the circumference of the exterior surface of the object to be viewed by a single camera; a set of four cameras (above, below, to the left of and to the right of the object) may be sequentially positioned to view the entire exterior surface of the object as it moves in the direction of arrow A, prior to exterior layer 16 fabrication.

Video sensor means 20 is connected via a cable 22 to a video display means 23, such as a TV monitor and the like, including a suitable video signal processing subsystem, as hereinafter more fully described, and an alarm means 24 for indicating that the processed video signal contains signal components attributable to a flaw 15 having parameters exceeding a predetermined set of flaw video characteristics.

The area on surface 14a viewable about sensor central axis 21 is preferably illuminated by a diffuse illumination means 28 comprising a light source 29, positioned substantially perpendicular to the object surface but slightly removed from axis 21, and an optical diffusing means 30 positioned between light source 29 and surface 14a and also removed from field of view axis 21 to prevent blockage thereof. Diffuse illumination source 28 provides a substantially uniform illumination of the entire object surface 14a within the field of view of the TV sensor 20 to facilitate a uniform response with minor variations in the texture of surface 14a.

A plurality of relatively intense illumination means 31a–31d and 32a–32d are respectively arranged on either side of optical path 21 with respect to the direction A of motion of the object to provide oblique illumination to facilitate specular reflection from the sides of grooves, pits, holes and perturbances classifiable as flaws. Each oblique illumination source means comprises a light source 33 and a suitable reflector means 34 for directing substantially all of the luminous output of each light source 33 toward cable surface 14a. Thus, in the illustrative embodiment, a first bank of oblique illumination means 31a–31d are arranged between the object and one side of a plane formed through optical axis 21 perpendicular to the direction of travel of the object, and a second bank of oblique illumination means 32a–32d (means 32b not shown for purposes of simplicity) are arranged upon the opposite side of the plane. All of oblique illumination sources 31a–31d and 32a–32d are arranged to direct their luminous outputs substantially upon that area on surface 14a within the field of view of video sensor 20.

Referring now to FIG. 2, wherein like reference designations are utilized for like elements, in another preferred embodiment, the oblique illumination means comprises a front member 40 positioned between the object 11 to be analyzed and a plurality of light sources 31' and 32' arranged to reflect their luminous output from the surface of front member 40 closest to object 11 onto that portion of the object surface 14a within the field of view of the sensor. Front member 40 has an aperture 41 formed therethrough centered on optical axis 21 to facilitate reception of reflected light by sensor 20 from the illuminated portion of object 11. Thus, the surface of front member 40 closest to object 11 typically has a white diffuse surface and oblique illumination means 31' and 32' are typically positioned above or below the object with their luminous output being directed against the diffuse surface of member 40 in such manner as to be reflected, as along optical paths 42 and 43, to illuminate a portion of surface 14a viewable by sensor 20.

The reflected light components received by sensor means 20 are converted into a video signal containing flow components and is available at sensor output 22 for subsequent processing. In one preferred embodiment, an analog-to-digital (A/D) converter means 50 receives the sensor output video signal for conversion to a stream of digital flaw data for subsequent digital processing by external means (not shown). The sensor video output signal is also made available to an analog video signal processing subsystem 51 comprising a signal processor means 52 for extracting those portions of the video signal produced responsive to surface flaws and for reducing or removing video signal portions indicative of acceptable, normal surface characteristics; an adjustable threshold means 53 for detecting a processed signal generated by a flaw exceeding a preselected amplitude and/or duration, and forming an output signal for triggering of alarm means 24. Advantageously, a multi-position switch means 55 is utilized to couple the CRT display means 23 to one of the available signals, including the sensor video output signal, on line 56; the processed video signal, on line 57; the output of the adjustable threshold means, on line 58; or a signal indicative of actuation of the alarm means, on line 59. As shown in FIG. 2, the signal processing subsection 51 is illustrated as being associated with a first channel (CH. 1) which, as previously mentioned, is utilized for flaw detection over only a portion of the circumference of object surface 14a; as hereinabove mentioned, additional video sensor means 20, each with an associated video signal processing subsystem 51, may be utilized to complete the inspection of the remaining portions of the object surface, with additional switch means 55 selectively coupling signal processing subsection signals to additional channel (CH. 2, CH. 3 and/or CH. 4) inputs to the display means, either simultaneously, sequentially or in any previously selected manner. It should be understood that the number of video sensors is dependent upon the surface area and shape of the object to be evaluated, with the illustrative four channel system being advantageously adapted for viewing of the four 90° circumferential segments of a cylindrical object.

Referring now to FIGS. 3 and 3a–3d, one preferred embodiment of signal processor means 52 comprises a cable edge detector means 60 having a first input 60a receiving the video signal from sensor output line 22; a baseline compensation means 61 having a first input 61a coupled to the output 60a of the cable edge detector; a difference signal means 62 having a first, non-inverting (+) input 62a receiving the video signal from sensor output 22 and a second, inverting (−) input 62b coupled to the output 61b of the base line compensation means. The output 62c of the difference signal means is suitably filtered and conditioned in a signal filtering and conditioning means 63 to form the flaw signal coupled to adjustable threshold means 53 and to switch means 55 via line 57.

In operation, the video signal (FIG. 3a, wherein the increasing video amplitude corresponds to increasing magnitudes of light reflected from the object surface, plotted with respect to time) has a somewhat symmetrical curvature, due to scattering of illumination away from optical axis 21 at the extremes of curvature of the viewable surface. If a flaw is present, the video signal includes a video portion 71 having an amplitude H attributable to the lesser or greater reflection of light from that flaw. Cable edge detector means 60 detects the leading edge of the video signal, at time $t_O$, to energize the output 60b thereof, to form an output signal 72 (FIG. 3b) maintained in its energized state until the cable edge detector means senses the end of a line scan across the optical field, at time $t_1$, causing the edge detector output 60b to be de-energized. Thus, the sinusoidal baseline curvature, due to the roundness of the cable in combination with the use of planar field optics in a lens 20a (FIG. 2) associated with the sensor, is converted into a rectangular "box car" waveform 72, having a time duration equal to the time duration of a video portion of each sensor scan line. The rectangular waveform is converted within baseline compensation means 61 into a curved waveform 73 (FIG. 3c) having curvature similar to that expected of video signal 70 for an acceptable "unflawed" surface and of equal time duration ($t_1 - t_0$). The non-processed video input (from sensor output 22) is coupled to the non-inverting input 62a of difference-signal formation means 62, while the compensation signal 73, having the expected curvature is coupled to the inverting input 62b of means 62 for subtraction from the sensor video signal. Thus, the normal-curved video signal portion 70 is removed, by subtraction of the compensation signal 73, at the output 63c of different signal means and a difference signal 74 (FIG. 3d) thereby formed essentially comprises only the video signal portion 74 attributable to light reflection from a surface flaw, e.g. 15a. The difference output amplitude voltage peak $V_{pk}$ is related to the magnitude H of the flaw video signal.

I have found that the recovered flaw signal 74, from at least one particular type of object (a cable) to be analyzed, contains a characteristic high frequency pulse front and often contains a group of pulses. Thus, for use with this particular type of cable, signal filtering and conditioning means 63 advantageously includes high-pass frequency filtering means and/or signal differentiating means to accentuate the flaw signal.

A clock signal, on a clock line 75 (FIG. 3), may be coupled to additional inputs of the cable detector means and the signal filtering and conditioning means to aid in video signal processing. In particular, blurring of the image displayed on means 23 often occurs due to the movement of the flaw during the time for a single horizontal scan of the TV sensor. This blur may be substantially eliminated through strobing of the lighting means during the camera frame retrace interval, with the strobe clock being utilized within the video processing subsystem 52 to reset detectors, re-establish initial filtering and conditioning conditions and the like, prior to each lighting pulse. The blurring may also be essentially alleviated through the use of line scanning, utilizing the motion of the moving cable to provide the horizontal scan of the displayed image, whereby the horizontal synchronization generator may provide the clock pulses on line 75 to perform a resetting function, a triggering function, or a triggering function with fixed or variable timing to minimize the blurring of the observable image. It should be understood that both the strobe and scan techniques can be utilized to minimize the blurring of discrete objects to be inspected, when a sequence of the discrete objects are moving past the video sensor.

While the present invention has been described with reference to several preferred embodiments thereof, many variations and modificatons will now become apparent to those skilled in the art. It is my intent, therefore, to be limited not by the present disclosure herein, but only by the scope of the appending claims.

What is claimed is:

1. A television inspection system for detecting flaws upon a surface of an object, said object surface having a known color and a known average reflectivity, comprising:
   a backing member positioned to one side of said object and having a surface of substantially the same color and average reflectivity as said object;
   first illumination means for directing light at least obliquely upon said object surface;
   video sensor means situated upon an opposite side of said object from said backing member for converting light reflected from said object surface to a video signal;
   second illumination means for diffusing light substantially perpendicular upon the portion of said object surface viewable by said video sensor means; and
   means for monitoring the video signal to cause an alarm to be activated in the event that a parameter of the video signal exceeds one of a preselected set of flaw characteristics.

2. A television inspection system as set forth in claim 1, wherein said first illumination means comprises a plurality of light sources arranged to directly obliquely illuminate a portion of said object surface closest to said video sensor means.

3. A television inspection system as set forth in claim 1, wherein said first illumination means comprises a front member positioned between said object and said video sensor means, said front member having an aperture formed therethrough to facilitate passage of reflected light from said object to said video sensor means; and at least one light source positioned to reflect the luminous output thereof from a surface of said front member closest to said object and onto said object surface.

4. A television inspection system as set forth in claim 3, wherein said front member surface closest to said object has a white diffuse finish.

5. A television inspection system as set forth in claim 1, wherein said video signal monitoring means comprises a signal processor means for at least reducing those portions of said video signal generated by normal surface characteristics to extract a flaw portion of said video signal produced responsive to surface flaws; adjustable threshold means for detecting the presence of a flaw portion exceeding one of said preselected set of flaw characteristics; and means triggered by said threshold means for causing an alarm whenever an undesired flaw is sensed.

6. A television inspection system as set forth in claim 5, wherein said signal processing means comprises object detector means receiving said video signal for forming an output waveform during a time interval in which said video signal from said object is present; a baseline compensation means for converting the output waveform from said object detector means to a waveform having a shape and amplitude substantially equal to that of a video signal obtainable from an acceptable object surface; and a difference signal formation means for subtracting the waveform of said baseline compensation means from said video signal.

7. A television inspection system as set forth in claim 6, wherein said signal processor means further includes means for filtering and conditioning the output of said difference signal formation means.

8. A television inspection system as set forth in claim 1, wherein said object is caused to move during said inspection; and said first illumination means is strobed to remove components of said video signal caused by motion of said object.

9. A television inspection system as set forth in claim 1, further comprising means for converting said video signal to a visible display.

10. A television inspection system as set forth in claim 9, wherein the motion of said object through the field of view of said video sensor means is utilized to generate a line scan upon said display means.

* * * * *